(12) United States Patent
Hachiya et al.

(10) Patent No.: US 10,898,600 B2
(45) Date of Patent: Jan. 26, 2021

(54) DISINFECTING METHOD AND DISINFECTING APPARATUS

(71) Applicant: PANASONIC INTELLECTUAL PROPERTY MANAGEMENT CO., LTD., Osaka (JP)

(72) Inventors: Yoshiaki Hachiya, Shiga (JP); Kazushige Sugita, Hyogo (JP); Takashi Maniwa, Osaka (JP); Makoto Yamada, Osaka (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 1 day.

(21) Appl. No.: 15/666,780

(22) Filed: Aug. 2, 2017

(65) Prior Publication Data

US 2018/0043044 A1 Feb. 15, 2018

(30) Foreign Application Priority Data

Aug. 10, 2016 (JP) .................................. 2016-157652
Mar. 15, 2017 (JP) .................................. 2017-050567

(51) Int. Cl.
*A61L 2/10* (2006.01)
*A61L 2/08* (2006.01)
*A61L 2/26* (2006.01)
*B01J 23/30* (2006.01)
*B01J 35/00* (2006.01)

(52) U.S. Cl.
CPC ................ *A61L 2/10* (2013.01); *A61L 2/088* (2013.01); *A61L 2/26* (2013.01); *A61L 2202/11* (2013.01); *A61L 2202/25* (2013.01); *B01J 23/30* (2013.01); *B01J 35/004* (2013.01)

(58) Field of Classification Search
CPC ............... A61L 2/10; A61L 2/088; A61L 2/26
See application file for complete search history.

(56) References Cited

U.S. PATENT DOCUMENTS

| 5,939,194 A | 8/1999 | Hashimoto et al. |
| 6,013,372 A | 1/2000 | Hayakawa et al. |
| 6,090,489 A | 7/2000 | Hayakawa et al. |
| 6,830,785 B1 | 12/2004 | Hayakawa et al. |

(Continued)

FOREIGN PATENT DOCUMENTS

| CN | 103959429 A | 7/2014 |
| CN | 104379994 A | 2/2015 |

(Continued)

OTHER PUBLICATIONS

Office Action issued in Chinese Counterpart Patent Appl. No. 201710665244.5, dated May 29, 2020, along with an English translation thereof.

(Continued)

*Primary Examiner* — Sean E Conley
(74) *Attorney, Agent, or Firm* — Greenblum & Bernstein, P.L.C.

(57) ABSTRACT

A disinfecting method includes irradiating fungi or bacteria with light including violet light having a light emission peak with (i) a full width at half maximum of at most 20 nm and (ii) a peak wavelength included in a range of from 380 nm to 410 nm, inclusive.

19 Claims, 12 Drawing Sheets

(56) References Cited

U.S. PATENT DOCUMENTS

| | | | |
|---|---|---|---|
| 2008/0119352 A1* | 5/2008 | Kitaguchi | B01D 53/8678 502/74 |
| 2008/0305004 A1 | 12/2008 | Anderson et al. | |
| 2009/0143842 A1* | 6/2009 | Cumbie | A61N 5/0616 607/88 |
| 2011/0085936 A1 | 4/2011 | Haytman et al. | |
| 2012/0313014 A1 | 12/2012 | Stibich et al. | |
| 2013/0303972 A1* | 11/2013 | Haytman | A61N 5/0624 604/21 |
| 2014/0303547 A1* | 10/2014 | Loupis | A61N 5/062 604/20 |
| 2015/0129781 A1 | 5/2015 | Kretschmann | |
| 2015/0182646 A1 | 7/2015 | Anderson et al. | |
| 2015/0190540 A1 | 7/2015 | Stibich et al. | |
| 2016/0129342 A1 | 5/2016 | Ozaki et al. | |
| 2016/0129432 A1 | 5/2016 | Ozaki et al. | |
| 2017/0263434 A1 | 9/2017 | Stibich et al. | |
| 2017/0312379 A1 | 11/2017 | Stibich | |
| 2018/0154027 A1 | 6/2018 | Anderson et al. | |
| 2019/0378706 A1 | 12/2019 | Stibich et al. | |

FOREIGN PATENT DOCUMENTS

| | | |
|---|---|---|
| JP | 3704817 B2 | 8/2005 |
| JP | 2006-200358 A | 8/2006 |
| JP | 2009-507525 A | 2/2009 |
| JP | 4279842 B2 | 3/2009 |
| JP | 2011-055898 A | 3/2011 |
| JP | 2014-136113 A | 7/2014 |
| JP | 2016-016114 A | 2/2016 |
| JP | 6097977 B2 | 3/2017 |
| WO | 2013/015442 A1 | 1/2013 |

OTHER PUBLICATIONS

Chinese Search Report issued in Chinese Counterpart Patent Appl. No. 201710665244.5 dated May 29, 2020, along with an English translation thereof.

Office Action issued in Japanese Counterpart Patent Appl. No. 2017-050567, dated Sep. 29, 2020.

\* cited by examiner

DRAIN PIPE

| UV-B | 260 μW/cm² | 130 μW/cm² | 60 μW/cm² | 30 μW/cm² | ≥ 10 μW/cm² | NO IRRADIATION |
|---|---|---|---|---|---|---|
| (i) 18 h IRRADIATION<br>TOTAL: 18 HOURS (18 HOURS FROM START) | | | | | | |
| (ii) 18 h IRRADIATION + 6 h NO IRRADIATION + 18 h IRRADIATION + 6 h NO IRRADIATION + 6 h IRRADIATION<br>TOTAL: 42 HOURS (54 HOURS FROM START) | EFFECT OBSERVED | EFFECT OBSERVED | EFFECT OBSERVED | EFFECT OBSERVED | | |
| (iii) 18 h IRRADIATION + 6 h NO IRRADIATION + 18 h IRRADIATION + 6 h NO IRRADIATION + 18 h IRRADIATION + 6 h NO IRRADIATION<br>TOTAL: 54 HOURS (72 HOURS FROM START) | EFFECT OBSERVED | EFFECT OBSERVED | EFFECT OBSERVED | EFFECT OBSERVED | | |
| (iv) 18 h IRRADIATION + 6 h NO IRRADIATION + 18 h IRRADIATION + 6 h NO IRRADIATION + 18 h IRRADIATION + 6 h NO IRRADIATION THEN, LEFT STANDING 40 h NO IRRADIATION<br>TOTAL: 94 HOURS (112 HOURS FROM START) | EFFECT OBSERVED | EFFECT OBSERVED | EFFECT OBSERVED | EFFECT OBSERVED | | |

DISINFECTING METHOD AND DISINFECTING APPARATUS

CROSS REFERENCE TO RELATED APPLICATION

This application claims the benefit of priority of Japanese Patent Application Number 2016-157652 filed on Aug. 10, 2016 and Japanese Patent Application Number 2017-050567 filed on Mar. 15, 2017, the entire contents of which are hereby incorporated by reference.

BACKGROUND

1. Technical Field

The present disclosure relates to disinfecting methods and disinfecting apparatuses using light irradiation.

2. Description of the Related Art

Molds appear in wet area facilities such as bathrooms or kitchens or in humid places such as ceiling spaces or under floors. In removing molds, for example, a technique which uses a photocatalyst is known. For example, Japanese Unexamined Patent Application Publication No. 2006-200358 (Patent Literature 1) discloses activating a photocatalyst by irradiating the photocatalyst with ultraviolet light to perform disinfecting and deodorizing by photocatalytic reaction.

SUMMARY

In the above-described conventional technique, however, the floors and walls that are irradiated with ultraviolet light must be configured using materials that are resistant to ultraviolet light. Furthermore, the photocatalyst needs to be applied in advance, and thus the environments in which the technique can be used are limited.

In view of this, the present disclosure provides a versatile disinfecting method and disinfecting apparatus.

A disinfecting method according to an aspect of the disclosure includes irradiating one of a fungus and a bacterium with light including violet light having a light emission peak with (i) a full width at half maximum of at most 20 nm and (ii) a peak wavelength included in a range of from 380 nm to 410 nm, inclusive.

Furthermore, a disinfecting apparatus according to an aspect of the disclosure includes a light source which irradiates one of a fungus and a bacterium with light having a light emission peak with (i) a full width at half maximum of at most 20 nm and (ii) a peak wavelength included in a range of from 380 nm to 410 nm, inclusive.

According to the present disclosure, it is possible to provide a versatile disinfecting method and disinfecting apparatus.

BRIEF DESCRIPTION OF DRAWINGS

The figures depict one or more implementations in accordance with the present teaching, by way of examples only, not by way of limitations. In the figures, like reference numerals refer to the same or similar elements.

FIG. 7 is a chart illustrating first experiment results of observing fungi/bacteria in the case where the fungi/bacteria are irradiated with varying intensities of the violet light according to Embodiment 1;

FIG. 12 is a chart illustrating results of observing fungi/bacteria in the case where the fungi/bacteria are irradiated with varying intensities of the UV-B light according to Embodiment 2;

DETAILED DESCRIPTION OF THE EMBODIMENTS

Hereinafter, a disinfecting method and a disinfecting apparatus according to embodiments of the present disclosure will be described in detail with reference to the drawings. It should be noted that each of the subsequently-described exemplary embodiments shows a specific example. Therefore, numerical values, shapes, materials, structural components, the arrangement and connection of the structural components, steps, and the sequence of the steps, etc. shown in the following exemplary embodiments are mere examples, and are not intended to limit the scope of the present disclosure. Furthermore, among the structural components in the following exemplary embodiments, components not recited in any one of the independent claims which indicate the broadest concepts of the present invention are described as arbitrary structural components.

Furthermore, the respective figures are schematic diagrams and are not necessarily precise illustrations. Therefore, for example, the scales, etc. in the respective figures are not necessarily uniform. Furthermore, in the respective figures, substantially identical components are assigned the same reference signs, and overlapping description thereof is omitted or simplified.

Embodiment 1

[Outline]

A disinfecting method and a disinfecting apparatus according to this embodiment realize disinfection by irradiating fungi/bacteria with light. It should be noted that, in this Specification, disinfection refers to suppressing the proliferation of fungi/bacteria. Specifically, disinfection means not only the destruction, extinction, or elimination of fungi/bacteria by decomposition, but also the suppression of growth or appearance of fungi/bacteria. Suppressing growth of fungi/bacteria includes not only causing complete stoppage of growth but also slowing down growth speed.

Figure 1:
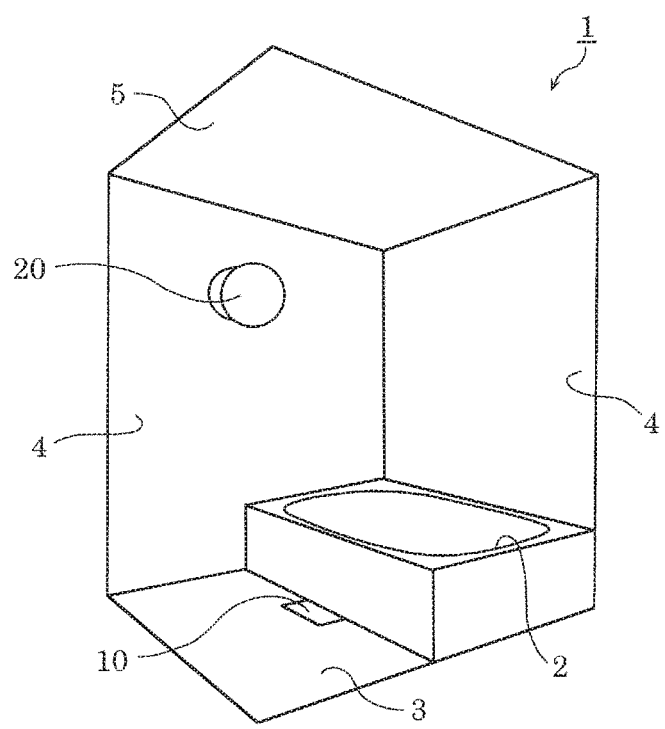
FIG. 1 is a schematic diagram of a bathroom to which a disinfecting apparatus according to Embodiment 1 is applied.
Figure 2:
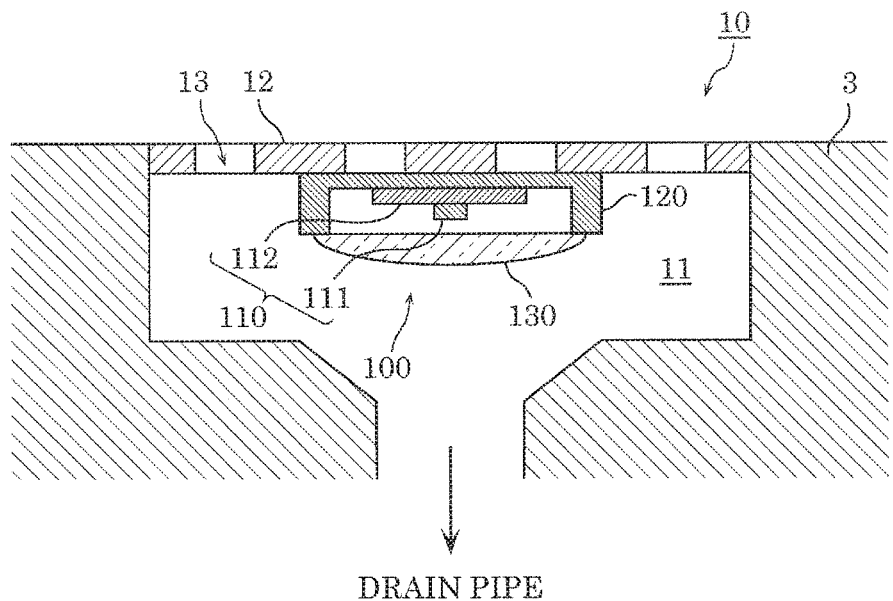
FIG. 2 is a cross-sectional view of a drainage port to which the disinfecting apparatus according to Embodiment 1 is installed.

FIG. 1 is a schematic diagram of bathroom 1 to which disinfecting apparatus 100 according to this embodiment is applied. FIG. 2 is a cross-sectional view of drainage port 10 to which disinfecting apparatus 100 according to this embodiment is installed.

Disinfecting apparatus 100 according to this embodiment is applied to a wet area facility such as bathroom 1 illustrated in FIG. 1. The wet area facility is not limited to bathroom 1 and may be a kitchen, a toilet, a wash basin, plumbing, etc. Furthermore, disinfecting apparatus 100 is applied not only to wet area facilities but also to humid places such as ceiling spaces or under floors.

Bathroom 1 illustrated in FIG. 1 is, for example, a bathroom module, and includes bath tub 1, floor 3, walls 4, and ceiling 5. Bath tub 2, floor 3, walls 4, and ceiling 5 are configured from components formed using resin material, etc. In this embodiment, the resin material used for bath tub 2, floor 3, walls 4, and ceiling 5 need not be resistant to ultraviolet light.

As illustrated in FIG. 1, drainage port 10 is provided in floor 3. As illustrated in FIG. 2, drainage port 10 includes water catching space 11 and lid 12. At least one through hole 13 is provided in lid 12. Water, etc., sprinkled on floor 3 flows into water catching space 11 via through hole 13, and is discharged to a drain pipe. It should be noted that a filter for removing trash, and so on, may be provided between water catching space 11 and the drain pipe.

In this embodiment, disinfecting apparatus 100 is installed on the underside of lid 12 of drainage port 10, as illustrated in FIG. 2. Disinfecting apparatus 100 irradiates the inside of water catching space 11 with light including violet light. Disinfecting apparatus 100 suppresses the growth of fungi/bacteria inside drainage port 10.

Specifically, the fungi/bacteria include true fungi (eumycetes) such as molds and yeasts or bacteria such as eubacteria. In this embodiment, true fungi are, for example, *cladosporium* (or *cladosporioides*), *rhodotorula*, etc. Bacteria are, for example, *Pseudomonas aeruginosa*. Disinfecting apparatus 100 suppresses the proliferation of true fungi such as *cladosporium* and *rhodotorula* as well as bacteria such as *Pseudomonas aeruginosa*.

It should be noted that the location at which disinfecting apparatus 100 is installed is not limited to the inside of drainage port 10. For example, as illustrated in FIG. 1, illumination apparatus 20 is installed in wall 4 of bathroom 1. Illumination apparatus 20 may be disinfecting apparatus 100. In other words, illumination apparatus 20 may emit light including violet light. In this case, illumination apparatus 20 may switch between emitting white light and violet monochromatic light. Accordingly, by having illumination apparatus 20 function as disinfecting apparatus 100, it is possible to suppress the growth of fungi/bacteria that can appear in bath tub 2, floor 3, wall 4, ceiling 5, etc.

[Configuration of Disinfecting Apparatus]

Figure 3:
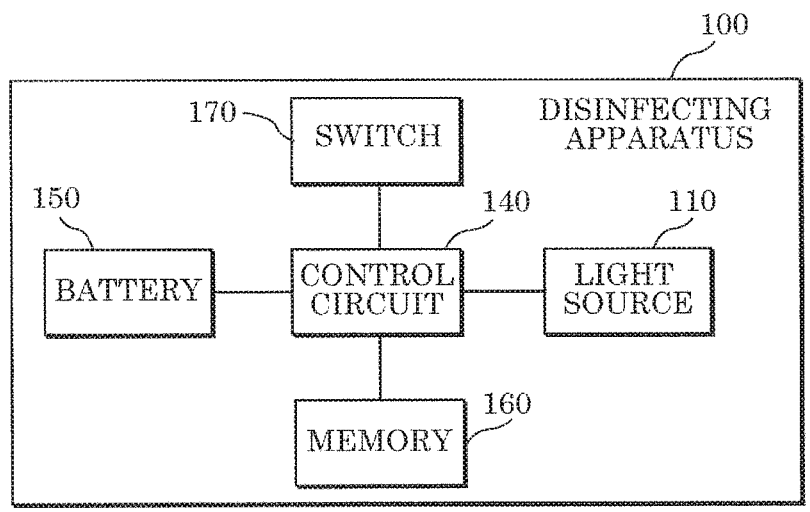
FIG. 3 is a block diagram illustrating a configuration of the disinfecting apparatus according to Embodiment 1.

Hereinafter, disinfecting apparatus 100 according to this embodiment will be described with reference to FIG. 2 and FIG. 3. FIG. 3 is a block diagram illustrating the configuration of disinfecting apparatus 100 according to this embodiment.

As illustrated in FIG. 2 and FIG. 3, disinfecting apparatus 100 includes light source 110 which emits light including violet light. Disinfecting apparatus 100 includes case 120 and optical component 130. Disinfecting apparatus 100 further includes control circuit 140, battery 150, memory 160, and switch 170.

Light source 110 is a light emitter which emits light including violet light. Light source 110 irradiates fungi/bacteria with the light including violet light. In this embodiment, light source 110 emits light including violet light, according to power supplied from battery 150.

As illustrated in FIG. 2, light source 110 light emitting diode (LED) 111 and board 112. Light source 110 is, for example, what is called a chip-on-board (COB) module in which a bare chip (LEI) 111 is directly mounted on board 112.

LED 111 is an example of a light-emitting element which emits light including violet light. LED 111 emits, for example, violet monochromatic light.

The violet light emitted by LED 111 has a light emission peak having a full width at half maximum of at most 20 nm. It should be noted that the full width at half maximum may be, for example, at most 15 nm or at most 10 nm.

The peak wavelength in the light emission peak of the violet light is included in a range of from 380 nm to 410 nm, inclusive. It should be noted that the peak wavelength may be in a range of, for example, 380 nm to 400 nm, inclusive. Moreover, the peak wavelength is the wavelength at the time when light emission intensity is largest (or maximum) in a spectral distribution of violet light.

Figure 4:
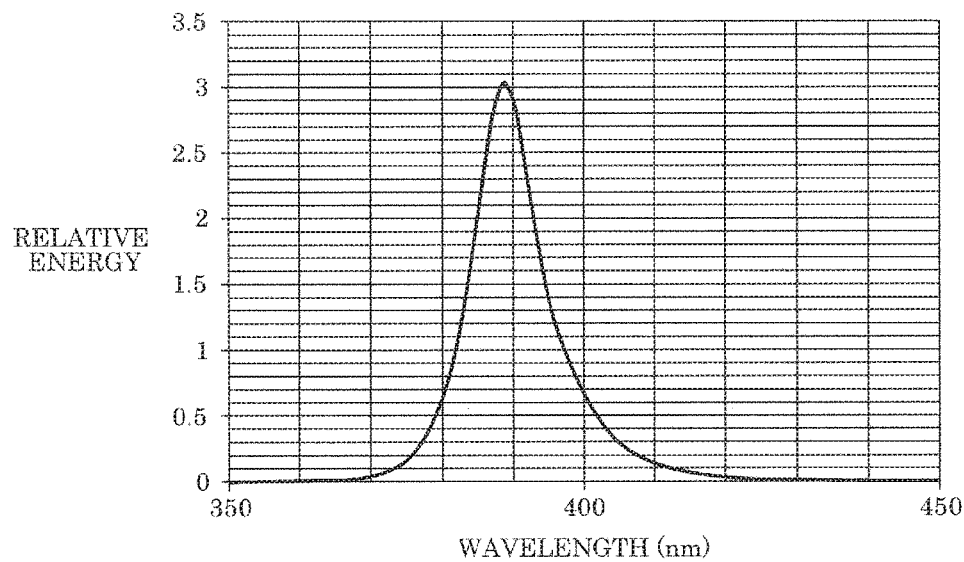
FIG. 4 is a graph illustrating a spectral distribution of violet light emitted by the disinfecting apparatus according to Embodiment 1.

LED 111 emits violet light with the spectral distribution illustrated in FIG. 4. FIG. 4 is a graph illustrating the spectral distribution of violet light emitted by disinfecting apparatus 100 according to this embodiment. It should be noted that, in FIG. 4, the horizontal axis represents wavelength and the vertical axis represents the relative energy (intensity) of light. As illustrated in FIG. 4, the violet light emitted by LED 111 has a peak wavelength of approximately 390 nm and a full width at half maximum of approximately 10 nm.

It should be noted that LED 111 may emit light including violet light and another wavelength component, instead of emitting violet monochromatic light. For example, LED 111 may emit visible light including blue light, green light, etc., aside from violet light. For example, LED 111 may emit white light.

For board 112, it is possible to use, for example, a ceramic board, a resin board, or a metal base board. Board 112 is fixed to the base of case 120. A metal wire (not illustrated in the figure) is provided to board 112.

For example, control circuit 140 for causing LED 111 to light up is provided on board 112, and LED 111 and battery 150 are connected via the metal wire. It should be noted that control circuit 140 may be formed as a separate body from light source 110.

It should be noted that light source 110 may be a surface mounted device (SMD) module. Specifically, a package-type LED element (SMD LED element) may be mounted on board 112. A package-type LED element includes, for example, a resin container having a cavity, an LED chip (LED 111) mounted inside the cavity, and a sealant which is filled into the cavity.

Furthermore, light source 110 may include a laser element, an organic electroluminescent (EL) element, etc., instead of LED 111. Alternatively, light source 110 may be a discharge lamp such as a fluorescent lamp.

Case 120 houses light source 110, control circuit 140, battery 150, and memory 160. Case 120 is formed using, for example, a resin material such as polybutylene terephthalate (PBT) or a metal material. Case 120 is, for example, a flat, bottomed, substantially cylindrical container, but the size and shape of case 120 are not limited to such.

Case 120 is fixed to the underside of lid 12 of drainage port 10 by using, for example, an adhesive sheet (not illustrated in the figure), etc. Specifically, case 120 is disposed with optical component 130 facing downward so that light is emitted downward. It should be noted that the method of fixing and the orientation of case 120 is not limited to such. For example, case 120 may be screwed to lid 12 or floor 3 (a constructional material such as a floor material making up the base of water catching space 11). Alternatively, case 120 may be placed on the base of water catching space 11 so as to emit light sideways.

Optical component 130 is located forward (i.e., on the light emission side) of light source 110, and is fixed to case 120. It should be noted that a gap between case 120 and optical component 130 may be sealed using a water-resistant adhesive, etc., in order to prevent the entry of moisture.

Optical component 130, for example, causes the light emitted by light source 110 to diffuse (scatter) and exit as diffused light. Accordingly, the entirety of water catching space 11 of drainage port 10 can be irradiated with the light emitted from optical component 130. It should be noted that optical component 130 may have a lens function for dispersing or condensing the light emitted by light source 110.

Optical component 130 may function as a filter which removes a predetermined wavelength component, for example. Specifically, optical component 130 may be an optical filter which removes, from the light emitted by light source 110, wavelength components in a range of from 350 nm to 380 nm, inclusive. In other words, optical component 130 may remove UV-A light. Furthermore, optical component 130 may remove UV-B light. Optical component 130 may remove the wavelength components other than violet light.

Here, remove means reducing the intensity of a wavelength component. Specifically, remove means not only completely removing (that is, making the intensity of a wavelength component 0) but also making the intensity of a wavelength component smaller than a predetermined threshold.

For example, if ultraviolet light is removed by optical component 130, substantially no ultraviolet light will be emitted to the outside of disinfecting apparatus 100. Accordingly, disinfecting apparatus 100 can be used even when the components to be irradiated (construction materials making up the inner face, etc., of drainage port 10) are not resistant to ultraviolet light. Therefore, the versatility of disinfecting apparatus 100 is enhanced.

Control circuit 140 controls the irradiation conditions of the light including violet light. For example, control circuit 140 controls the irradiation period, the irradiation start (or stop) timing, and the irradiation method (light distribution, etc.). Specifically, control circuit 140 controls the lighting-up and putting-out of light source 110. Control circuit 140 causes LED 111 to light up by supplying LED 111 with power supplied from battery 150. Control circuit 140 is, for example, a microcontroller.

Control circuit 140 controls the lighting-up and putting-out of light source 110 based on, for example, schedule information stored in memory 160. Specifically, control circuit 140 may have a timer function. For example, control circuit 140 causes the irradiation of violet light from light source 110 to continue during a predetermined first period (an irradiation period), and subsequently causes the irradiation of violet light from light source 110 to stop during a predetermined second period (a non-irradiation period). Control circuit 140 may control light source 110 to alternately repeat the irradiation period and the non-irradiation period. Accordingly, light irradiation and non-irradiation can be performed appropriately, and thus the disinfecting effect can be enhanced.

Furthermore, control circuit 140 may control the lighting-up and putting-out of light source 110 based on an operation signal transmitted from switch 170. Accordingly, it is possible to cause light source 110 to light up to carry out disinfection at the timing at which a user operates switch 170, that is, at the timing desired by the user.

Battery 150 is a detachable power source. Battery 150 is housed in a housing (not illustrated in the figure) provided in case 120, and supplies power to light source 110 via control circuit 140. Battery 150 is a primary power source such as an alkaline battery or a manganese battery, but is not limited to such. Battery 150 may be a rechargeable secondary power source.

Memory 160 is a non-volatile memory in which a light irradiation program and schedule information, etc., are stored. The schedule information indicates, for example, the start timing and end timing of light irradiation. The schedule information may indicate the lengths of each of an irradiation period and a non-irradiation period.

Control circuit 140, for example, reads the irradiation program and the schedule information from memory 160, and controls the lighting-up and putting-out of light source 110 based on the irradiation program and the schedule information that are read.

Switch 170 is a switch for switching between light irradiation and non-irradiation. Switch 170 is, for example, provided exposed to the outside of case 120, and can be operated by a user.

First Experiment

Next, a first experiment performed to study the relationship between the wavelength of light with which true fungi, out of the fungi/bacteria, is irradiated and the growth of the true fungi will be described. The fungi/bacteria subjected to the first experiment are *cladosporium* and *rhodotorula*.

In the first experiment, violet light and UV-A light are used as the light with which the fungi/bacteria are irradiated. First, each light will be described.

As previously described, the violet light is light having the spectral distribution illustrated in FIG. 4. Specifically, the violet light is a violet monochromatic light having a peak wavelength of approximately 390 nm and a light emission peak having a full width at half maximum of approximately 10 nm.

Figure 5:
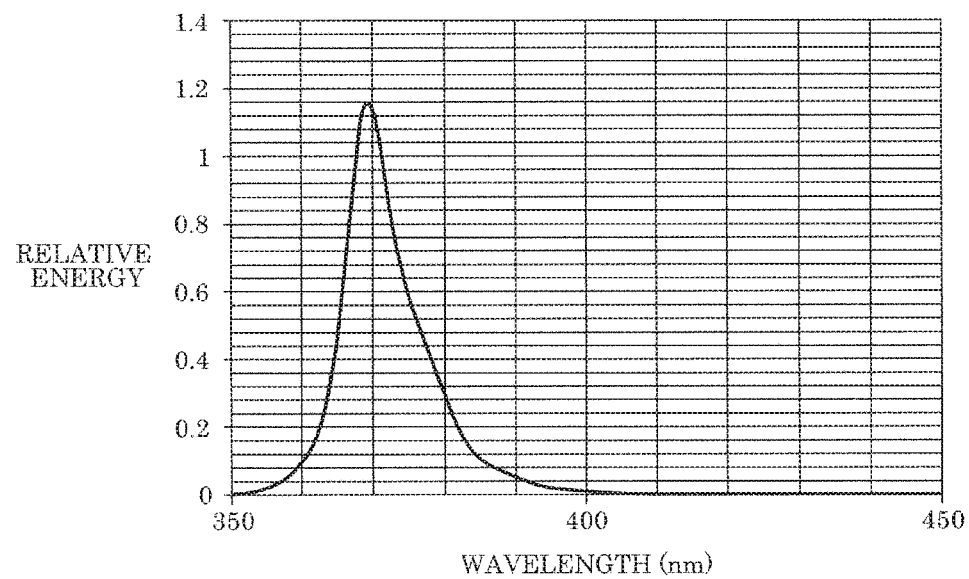
FIG. 5 is a graph illustrating a spectral distribution of UV-A light used as a comparative example in Embodiment 1.

The UV-A light is light having the spectral distribution illustrated in FIG. 5. FIG. 5 is a graph illustrating the spectral distribution of the UV-A light that is used as a comparative example in this embodiment. It should be noted that, in FIG. 5, the horizontal axis represents wavelength and the vertical axis represents the relative energy (intensity) of light. As illustrated in FIG. 5, the UV-A light has a light emission peak in which the peak wavelength is included in a range of from 350 nm to 380 nm, inclusive. The full width at half maximum is approximately 10 nm.

(Violet Light Irradiation)

Figure 6:
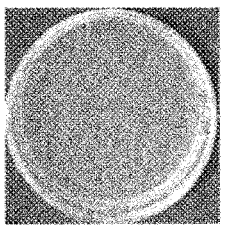
FIG. 6 is a chart illustrating results of observing fungi/bacteria in the case where the fungi/bacteria are irradiated with the UV-A light and the violet light according to Embodiment 1.

First, the state of the fungi/bacteria when irradiated with the violet light will be described below with reference to FIG. 6. FIG. 6 is a chart illustrating results of observing fungi/bacteria in the case where the fungi/bacteria are irradiated with each of the UV-A light and the violet light according to this embodiment.

Observation was carried out by verifying Petri dishes from above by visual inspection (specifically, by imaging using a camera). FIG. 6 illustrates the images of the Petri dishes that were taken.

It should be noted that, in FIG. 6, the small spots are *rhodotorula* and the paste-like forms are *cladosporium*. This is the same in FIG. 7, FIG. 12, and FIG. 14 described later.

In the experiment, light irradiation and non-irradiation were performed repeatedly, for predetermined time periods each, on predetermined amounts of *cladosporium* and *rhodotorula* that were cultured in mediums in the Petri dishes, and the state of the fungi/bacteria was observed at predetermined timings. The light irradiation time was set to 18 hours and the non-irradiation time was set to 6 hours. The intensity of the violet light during irradiation was 3000 µW/cm$^2$. It should be noted that this value was the value measured using a Konica Minolta UM-360.

(i) The first observation was performed after light irradiation was performed initially for 18 hours (i.e., at the point in time when total irradiation time was 18 hours, and 18 hours had elapsed from the start).

(ii) The second observation was performed 6 hours after light irradiation was started after 6 hours of non-irradiation, 18 hours of irradiation, and 6 hours of non-irradiation were performed sequentially after the first observation (i.e., at the point in time when total irradiation time was 42 hours, and 54 hours had elapsed from the start).

(iii) The third observation was performed at the point when 12 hours of irradiation and 6 hours of non-irradiation were performed after the second observation (i.e., at the point in time when total irradiation time was 54 hours, and 72 hours had elapsed from the start).

(iv) The fourth observation was performed at the elapse of 40 hours of non-irradiation after the third observation (i.e., at the point in time when total irradiation time was 54 hours, and 112 hours had elapsed from the start).

Furthermore, as a comparative example, observations were carried out at the same timings as (i) to (iv) above, in the state where absolutely no light irradiation was carried out ("NO IRRADIATION" in FIG. 6).

As illustrated in FIG. 6, when light irradiation is not performed, a thin growth of *cladosporium* was verified after 18 hours. Subsequently, growth of both *cladosporium* and *rhodotorula* was verified with the passing of time.

In contrast, when violet light irradiation was performed, growth of *cladosporium* and *rhodotorula* could not be verified by visual inspection in any of the following cases: after 18 hours, after 54 hours, and after 72 hours from start. In this manner, it can be seen that the growth of *cladosporium* and *rhodotorula* was suppressed by irradiation with violet light.

Furthermore, a small amount of *cladosporium* and *rhodotorula* was verified after 112 hours from the start, at the point in time when 46 hours had elapsed from the last irradiation. Therefore, it can be seen that violet light did not cause total extinction of *cladosporium* and *rhodotorula*.

As described above, irradiation with violet light can suppress growth without causing the extinction of fungi/ bacteria such as *cladosporium* and *rhodotorula*. As such, even if violet light irradiation is carried out, extinction of beneficial fungi/bacteria does not occur, and thus the fungi/ bacteria can be made to coexist. Causing extinction of beneficial fungi/bacteria may bring about faster-than-normal growth of harmful fungi/bacteria. Therefore, according to this embodiment, suppression of growth is possible without causing extinction of fungi/bacteria, and, as a result, the disinfecting effect can be enhanced.

It should be noted that because the fungi/bacteria are not killed off even when irradiated with violet light, the growth of the fungi/bacteria will advance if violet light irradiation is not performed for a long time. As in (iii) in FIG. 6, however, even at the elapse of 6 hours of non-irradiation after violet light irradiation, the growth of *cladosporium* and *rhodotorula* was sufficiently suppressed. In other words, it can be seen that violet light irradiation need not be performed constantly. As such, for example, by repeating violet light irradiation and non-irradiation, a sufficient disinfecting effect can be obtained while reducing power consumption.

(UV-A LIGHT Irradiation)

Next, the state of fungi/bacteria when irradiated with UV-A light instead of violet light will be described with reference to FIG. 6. The UV-A light used here has the spectral distribution illustrated in FIG. 5. The experiment conditions are the same as those in the case of the violet light described above. Here, observations were carried out for two cases, that is, the case of high intensity UV-A light irradiation and the case of low intensity UV-A light irradiation. Specifically, the intensities of the UV-A light during irradiation were 270 µW/cm$^2$ and 100 µW/cm$^2$. It should be noted that these values were the values measured using a Topcon UVR2.

Regardless of the intensity of UV-A light, growth of both *cladosporium* and *rhodotorula* was verified with the passing of time. It can be seen that growth of fungi/bacteria was suppressed compared to when light irradiation is not performed, but the growth suppressing effect is low compared to when violet light irradiation was performed.

It is generally known that ultraviolet light has a bactericidal effect. Based on the above-described experiment results, however, it can be seen that even if fungi/bacteria are irradiated with UV-A light, the fungi/bacteria suppression effect was not sufficient. Therefore, for example, by using the power required to emit UV-A light to emit violet light instead, suppression of fungi/bacteria growth can be effectively implemented.

(Violet Light Intensity)

Based on the above-described experiment results, it can be seen that a suppressing effect on fungi/bacteria growth can be obtained by irradiation with violet light. In view of this, the results of an experiment verifying the relationship between violet light irradiation intensity and fungi/bacteria growth suppressing effect is described below.

Figure 7:
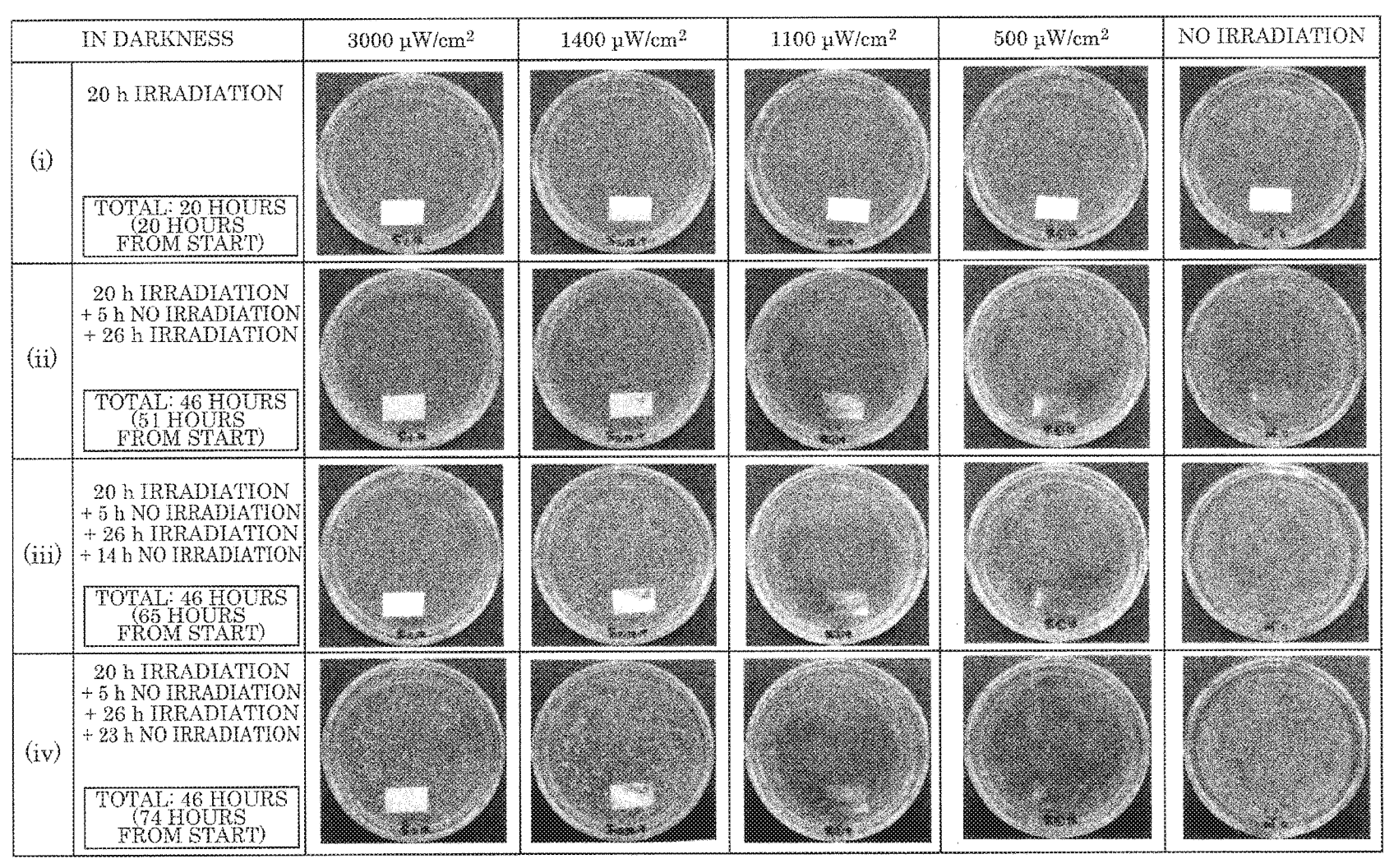

FIG. 7 is a chart illustrating results of observing fungi/ bacteria in the case where the fungi/bacteria are irradiated with varying intensities of the violet light according to this embodiment. Here, observation of fungi/bacteria was performed under conditions different from those in the experiment illustrated in FIG. 6. Specific details are as described below.

(i) The first observation was performed after violet light irradiation was performed initially for 20 hours (i.e., at the point in time when total irradiation time was 20 hours, and 20 hours had elapsed from the start).

(ii) The second observation was performed at the point in time when 26 hours of irradiation was performed after 5 hours of non-irradiation (left standing) after the first observation (i.e., at the point in time when total irradiation time was 46 hours, and 51 hours had elapsed from the start).

(iii) The third observation was performed at the point in time when 14 hours of non-irradiation had elapsed after the second observation (i.e., at the point in time when total irradiation time was 46 hours, and 65 hours had elapsed from the start).

(iv) The fourth observation was performed at the point in time when a further 9 hours of non-irradiation had elapsed after the third observation (i.e., at the point in time when total irradiation time was 46 hours, and 74 hours had elapsed from the start).

The intensities of the irradiated violet light were 3000 $\mu W/cm^2$, 1400 $\mu W/cm^2$, 1100 $\mu W/cm^2$, and 500 $\mu W/cm^2$. It should be noted that these values were the values measured using a Konica Minolta UM-360. Furthermore, the case where light irradiation is not performed is also shown as a comparative example.

As illustrated in FIG. 7, it can be seen that the fungi/bacteria suppressing effect is different depending on the intensity of the violet light during irradiation. Specifically, in the respective observation instances, it can be seen that the higher the intensity of the violet light, the more the growth of *cladosporium* and *rhodotorula* is suppressed. Furthermore, even in the cases where the samples were left standing with no irradiation after violet light irradiation, it can be seen that the appearance of *cladosporium* and *rhodotorula* was suppressed more when irradiation was performed with violet light of higher intensity.

Second Experiment

Next, a second experiment performed to study the relationship between the wavelength of light with which bacteria, out of the fungi/bacteria, is irradiated and the growth of the bacteria will be described. The fungus subjected to the second experiment is *Pseudomonas aeruginosa*. It should be noted that the second experiment was also performed in the same manner on *rhodotorula* (*rhodotorula*) to also verify the reliability of the first experiment results.

(Experiment Conditions)

The preparation of the test bacterial culture was carried out as indicated below. For the *Pseudomonas aeruginosa*, a frozen strain is cultured for two days at 36±2° C. on triptic soy agar (Difco, hereafter referred to as TSA) plating medium. For the *rhodotorula*, a frozen strain is cultured for two days at 26±2° C. on potato dextrose agar (Nissui Pharmaceutical Co., Ltd., PDA). Each developed colony was scraped and prepared to approximately 10⁴ CFU/mL in sterilized ion exchange water to thereby obtain a test bacterial culture.

In addition, by filtering 1 mL of the test bacterial culture through a ¼ cut of a membrane filter, approximately 10⁴ CFU of bacteria were caught in the filter to thereby obtain a specimen. Each specimen was placed on the surface of a moisture retaining agar medium (1.5% agar medium) in a Petri dish, and the light irradiation test was performed. It should be noted that a specimen for keeping in darkness with no light irradiation was also prepared as a comparative example.

For the light with which the fungi/bacteria were irradiated, as in the first experiment, a violet monochromatic light having a peak wavelength of 390 nm and a light emission peak having a full width at half maximum of approximately 10 nm, as illustrated in FIG. 4, was used. Irradiation was carried out using violet light of three different intensities. Specifically, the irradiation intensities were set to 200 $\mu W/cm^2$, 1000 $\mu W/cm^2$, 2000 $\mu W/cm^2$, in the state where a moisture retaining quartz glass plate was placed on the Petri dish. It should be noted that actual measured values of the irradiation intensities measured using a Konica Minolta UM-360 were 200 $\mu W/cm^2$, 1100 $\mu W/cm^2$, 2400 $\mu W/cm^2$. The violet light irradiation times were continuous 24 hours and 48 hours.

The bacterial count measurement after the end of light irradiation was performed as indicated below. First, the specimen is collected in a stomacher plastic pouch containing 10 mL of a soya casein digest lecithin polysorbate (SCDLP) broth medium (Eiken Chemical Co., Ltd.) in advance, and homogenized using a Stomacher (Organo Co.) for two minutes to wash out the test bacteria from the specimen. The liquid that was washed out is used as the sample solution for bacterial count measurement.

From the sample solution, 10-fold serial dilution samples are made using physiological saline, and culturing for each bacteria is performed after 1 mL each of the stock solution and the diluted solutions are transferred into Petri dishes. Specifically, *Pseudomonas aeruginosa* is mixed with approximately 20 mL of TSA, then solidified and cultured for 48 hours at 36±2° C. *Rhodotorula* is mixed with approximately 20 mL of PDA, then solidified and cultured for three to five days at 26±2° C. After culturing, the bacterial count per specimen is obtained by counting the colonies developed in each of the mediums. It should be noted that a plurality of specimens are used under each condition, and the bacterial count is the average value of the bacterial counts of the respective specimens under the same condition, or in other words, the average bacterial count.

(Experiment Results)

Figure 8:
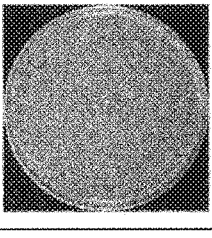
FIG. 8 is a chart illustrating test results in the case where *Pseudomonas aeruginosa* is irradiated with varying intensities of the violet light according to Embodiment 1.
Figure 9:
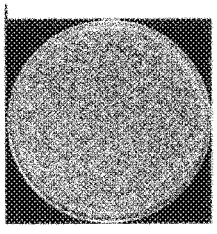
FIG. 9 is a chart illustrating test results in the case where *rhodotorula (rhodotorula)* is irradiated with varying intensities of the violet light according to Embodiment 1.

Hereinafter, the experiment results of the second experiment will be described with reference to FIG. 8 and FIG. 9. FIG. 8 is a chart illustrating test results in the case where *Pseudomonas aeruginosa* was irradiated with varying intensities of the violet light according to this embodiment. FIG. 9 is a chart illustrating test results in the case where *rhodotorula* was irradiated with varying intensities of the violet light according to this embodiment. FIG. 8 and FIG. 9 show images of the mediums in which the sample solutions for bacterial count measurement were cultured. Since the initial state in the violet light irradiation is the same as the initial state in darkness, illustration is omitted.

As illustrated in FIG. 8, when violet light irradiation was performed, almost no proliferation of *Pseudomonas aeruginosa* could be verified. Specifically, in each of the cases of irradiation intensity at 200 $\mu W/cm^2$, 1000 $\mu W/cm^2$, and 2000 $\mu W/cm^2$, the average bacterial count was a value smaller than 10 CFU per specimen.

In contrast, under condition of darkness, it was observed that *Pseudomonas aeruginosa* proliferated with the passing of time. Specifically, the average bacterial count after 24 hours of irradiation was $4.0 \times 10^5$ CFU, and the average bacterial count after 48 hours of irradiation was $9.7 \times 10^5$ CFU.

Based on the above, it can be seen that, by irradiating the *Pseudomonas aeruginosa* with violet light, the bacterial count of *Pseudomonas aeruginosa* was reduced, that is, *Pseudomonas aeruginosa* were being destroyed. It can be seen that aside from suppressing the growth of *Pseudomonas aeruginosa*, violet light also has a bactericidal effect.

In the same manner, as illustrated in FIG. 9, it was observed that, when violet light irradiation was performed, there was a difference in bactericidal effect according to irradiation intensity. Specifically, when irradiation intensity was 200 µW/cm², the average bacterial count after 24 hours of irradiation was 1.3×10⁵ CFU, and the average bacterial count after 48 hours of irradiation was 1.6×10⁵ CFU. In this manner, it can be seen that when irradiation intensity was 200 µW/cm², *rhodotorula* was not destroyed.

On the other hand, when irradiation intensity was at 1000 µW/cm² and 2000 µW/cm², the average bacterial counts were values smaller than 10 CFU per specimen. In other words, it can be seen that by irradiating with high intensity violet light, *rhodotorula* were destroyed.

Under condition of darkness, it was observed that *rhodotorula* proliferated, in the same manner as when irradiation intensity was low. Specifically, the average bacterial count after 24 hours of irradiation was 1.9×10⁵ CFU, and the average bacterial count after 48 hours irradiation was 4.6×10⁵ CFU. In either case, the average bacterial count was larger than when irradiation intensity was at 200 µW/cm². Based on this, it can be seen that irradiation with violet light, even at a low irradiation intensity, suppresses the proliferation of *rhodotorula*.

Based on the above, it can be seen that, by irradiating *rhodotorula* with violet light, the proliferation, that is, the growth of *rhodotorula* can be suppressed. Although *rhodotorula* cannot be destroyed when irradiation intensity is low, the disinfecting effect is manifested by suppressing growth. When irradiation intensity is high, *rhodotorula* can be destroyed. For example, when *rhodotorula* is irradiated with violet light at an irradiation intensity of at least 200 µW/cm², growth of *rhodotorula* can be suppressed. In addition, when *rhodotorula* is irradiated with violet light at an irradiation intensity of at least 1000 µW/cm2, destruction of *rhodotorula* can be carried out.

It should be noted that the first experiment yielded a result that *rhodotorula* does not become completely extinct even when irradiation intensity is high. In contrast, the second experiment yielded a result in which almost all the *rhodotorula* were destroyed.

This difference in the results is presumed to be due to the difference in the violet light irradiation method. Specifically, whereas violet light irradiation and non-irradiation were repeated in the first experiment, in the second experiment, continuous violet light irradiation was carried out, and no non-irradiation period was provided. Specifically, it is thought that, in the first experiment, bacteria proliferated in the non-irradiation periods. Based on this, it can be seen that continuous irradiation with violet light allows for more effective suppression of bacterial growth.

It should be noted that, as shown in the first experiment, even when violet light irradiation is performed intermittently, a fungi/bacteria growth suppressing effect, that is, a bactericidal effect is obtained. Therefore, in the case of intermittent irradiation, fungi/bacteria growth can be suppressed while reducing power consumption.

Advantageous Effects, Etc

As described above, the disinfecting method according to this embodiment includes irradiating fungi/bacteria with light including violet light having a light emission peak with (i) a full width at half maximum of at most 20 nm and (ii) a peak wavelength included in a range of from 380 nm to 410 nm, inclusive.

Accordingly, as illustrated in FIG. 6, irradiation with violet light enables the growth of fungi/bacteria to be suppressed. The violet light is visible light, and has less negative effects on the environment and organisms such as the human body compared to ultraviolet light. Therefore, components using a resin material, etc., having no ultraviolet light resistance can be irradiated with violet light, and growth of fungi/bacteria can be suppressed. Furthermore, since a photocatalyst is not used, there is no need to apply a photocatalyst in advance, and use in a place where a photocatalyst cannot be applied is possible. In this manner, according to this embodiment, a versatile disinfecting method can be provided.

Furthermore, unlike ultraviolet light, violet light can suppress the growth of fungi/bacteria but does not cause extinction of the fungi/bacteria. As such, when violet light irradiation is performed, beneficial fungi/bacteria do not become extinct. In other words, coexistence of fungi/bacteria is possible. Accordingly, since beneficial fungi/bacteria can also suppress the growth of harmful fungi/bacteria, the disinfecting effect can be further enhanced.

Furthermore, for example, the light with which the fungi/bacteria is irradiated, does not include UV-A light having a light emission peak with a peak wavelength included in a range of from 350 nm to 380 nm, inclusive.

Accordingly, since UV-A light which does not have a suppressing effect on the growth of fungi/bacteria is not included, the growth of fungi/bacteria can be effectively suppressed, as illustrated in FIG. 6, etc. For example, the power inputted to light source 110 can be used efficiently in violet light irradiation, without being used in UV-A light irradiation which does not contribute to disinfection. In this manner, it is possible to reduce the power consumption required in executing the disinfecting method, and thus realize energy conservation.

Furthermore, for example, in the irradiating, irradiation with the violet light and non-irradiation are repeated.

Accordingly, by providing a period in which violet light irradiation is not performed, growth of fungi/bacteria can be suppressed while suppressing power consumption.

Furthermore, for example, the fungi are *cladosporium* or *rhodotorula*.

Accordingly, it is possible to effectively suppress the growth of *cladosporium, rhodotorula*, etc., which tend to appear in wet area facilities such as bathrooms or kitchens or in humid places such as in ceiling spaces or under floors.

Furthermore, the bacterium is *Pseudomonas aeruginosa*.

When a person with compromised immunity is exposed to *Pseudomonas aeruginosa*, there is the risk of contracting *Pseudomonas aeruginosa* infection. Disinfecting apparatus 100 according to this embodiment can suppress the growth of *Pseudomonas aeruginosa*, and is therefore useful in preventing disease.

Furthermore, for example, disinfecting apparatus 100 according to this embodiment includes light source 110 which irradiates fungi/bacteria with light having a light emission peak with (i) a full width at half maximum of at most 20 nm and (ii) a peak wavelength included in a range of from 380 nm to 410 nm, inclusive.

Accordingly, as in the above-described disinfecting method, irradiation with violet light enables the growth of fungi/bacteria to be suppressed.

Furthermore, for example, further includes an optical filter (optical component 130) which is disposed between light source 110 and the fungi/bacteria, and removes, from the light emitted by light source 110, wavelength components in a range of from 350 nm to 380 nm, inclusive.

Accordingly, it is possible to prevent the emission of UV-A light which has no suppressing effect on the growth of fungi/bacteria. Therefore, since it is possible to prevent deterioration of a component to be irradiated due to UV-A light, disinfecting apparatus 100 can be used in various places. In other words, a versatile disinfecting apparatus 100 can be provided.

Embodiment 2

A disinfecting method according to Embodiment 2 irradiates fungi/bacteria with not only violet light but also UV-B light out of ultraviolet light. By using UV-B light, the disinfecting effect can be further enhanced. Furthermore, in this embodiment, although versatility is reduced somewhat because a component to be irradiated needs to have ultraviolet light resistance in order for ultraviolet to be used, versatility can be enhanced in terms of not using a photocatalyst. Hereinafter, details of the disinfecting method and disinfecting apparatus which executes the disinfecting method according to this embodiment will be described.

[Configuration of Disinfecting Apparatus]

Figure 10:
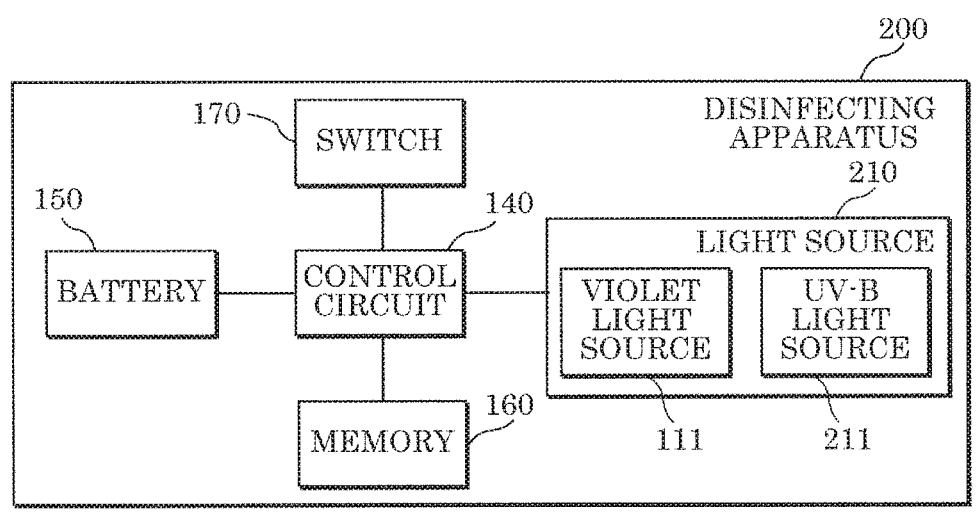
FIG. 10 is a block diagram illustrating a configuration of a disinfecting apparatus according to Embodiment 2.

FIG. 10 is a block diagram illustrating the configuration of disinfecting apparatus 200 according to this embodiment. Compared to disinfecting apparatus 100 according to Embodiment 1 illustrated in FIG. 3, disinfecting apparatus 200 is different in including light source 210 and control circuit 240 in place of light source 110 and control circuit 140. Hereinafter, description will be carried out focusing on the points of difference with Embodiment 1, and description of common points may be omitted or simplified.

Light source 210 includes violet light source 211 and UV-B light source 212.

Violet light source 211, for example, emits violet light having the spectral distribution indicated in FIG. 4, as in Embodiment 1. Violet light source 211 is, for example, LED 111 in Embodiment 1.

UV-B light source 212 is an example of a light source that emits light including UV-B light. UV-B light source 212 is, for example, a fluorescent lamp that emits UV-B light, but is not limited to such. For example, UV-B light source 212 may be a xenon lamp, a metal halide lamp, etc., and may be a solid-state light emitting element such as an LED or a laser element.

Figure 11:
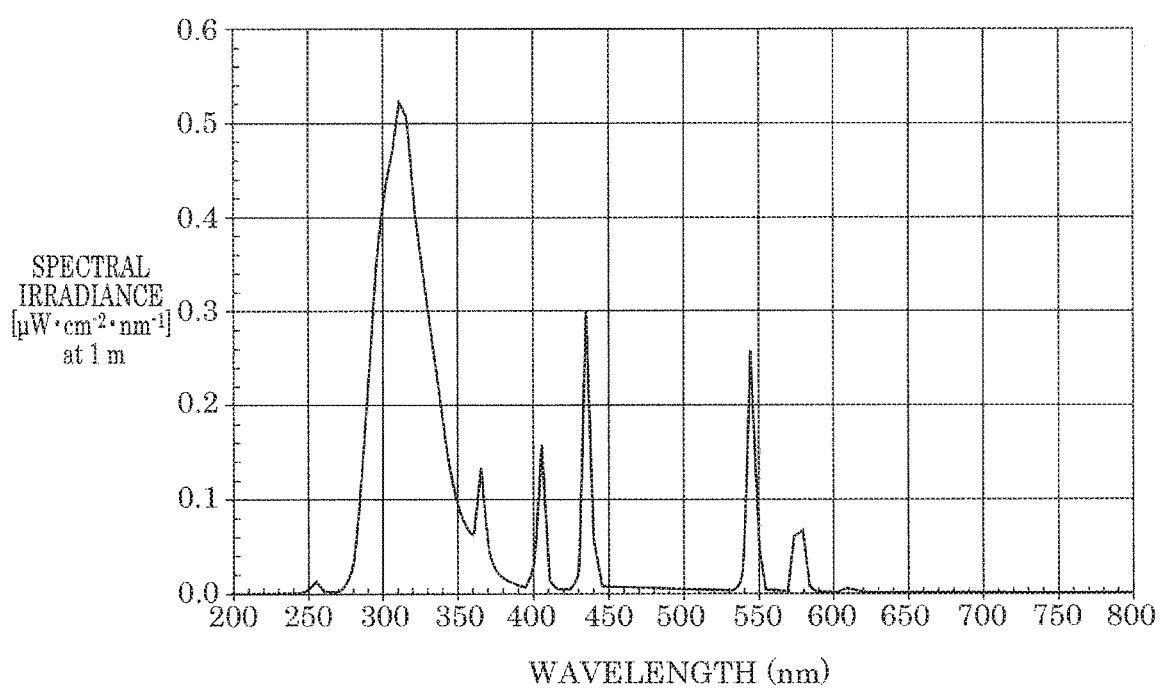
FIG. 11 is a graph illustrating a spectral distribution of UV-B light emitted by the disinfecting apparatus according to Embodiment 2.

UV-B light source 212, for example, emits UV-B light having the spectral distribution illustrated in FIG. 11. FIG. 11 is a graph illustrating the spectral distribution of the UV-B light emitted by disinfecting apparatus 200 according to this embodiment. It should be noted that, in FIG. 11, the horizontal axis represents wavelength and the vertical axis represents spectral irradiance (equivalent to light intensity) at a point that is 1 m in front of UV-B light source 212.

With the UV-B light emitted by UV-B light source 212, the peak wavelength in the maximum light emission peak is included in a range of from 280 nm to 350 nm, inclusive, as illustrated in FIG. 11. It should be noted that it is acceptable for the UV-B light to have only a single light emission peak as illustrated in FIG. 4, FIG. 5, etc.

Control circuit 240 individually controls the violet light irradiation conditions and the UV-B light irradiation conditions. Specifically, control circuit 240 individually controls the lighting-up and putting-out of each of violet light source 211 which emits the violet light and UV-B light source 212 which emits the UV-B light. For example, control circuit 240 controls the light-up period, the light-up start (or stop) timing, and the light-up method (light distribution, etc.) of violet light source 211. For example, control circuit 240 controls the light-up period, the light-up start (or stop) timing, and the light-up method (light distribution, etc.) of UV-B light source 212. Accordingly, disinfection apparatus 200 can switch the light with which the fungi/bacteria are to be irradiated between violet light and UV-B light.

In this embodiment, control circuit 240 mutually exclusively causes violet light source 211 and UV-B light source 212 to light up. For example, control circuit 240 reads schedule information stored in memory 160 and controls the lighting-up and putting-out of violet light source 211 according to the schedule indicated in the schedule information that was read. Furthermore, when switch 170 is operated, control circuit 240 controls the lighting-up and putting-out of UV-B light source 212. Accordingly, destruction of fungi/bacteria by UV-B light irradiation can be carried out at an arbitrary timing as necessary while suppressing growth of fungi/bacteria by violet light irradiation.

[Experiment Results]

Next, the results of an experiment performed in order to study the relationship between the intensity of UV-B light with which fungi/bacteria is irradiated and the growth of the fungi/bacteria will be described. In this experiment, UV-B light having the spectral distribution illustrated in FIG. 11 was used as the light with which the fungi/bacteria are irradiated.

FIG. 12 is a chart illustrating results of observing fungi/bacteria in the case where the fungi/bacteria are irradiated with varying intensities of the UV-B light according to this embodiment. The UV-B light used here has the spectral distribution illustrated in FIG. 11. The experiment conditions are the same as those in the case of the violet light described above.

Here, the intensities of the UV-B light are at 260 $\mu W/cm^2$, 160 $\mu W/cm^2$, 60 $\mu W/cm^2$, 30 $\mu W/cm^2$, and 10 $\mu W/cm^2$ or lower. It should be noted that these values were the values measured using a Topcon UVR2. Here, although FIG. 12 also illustrates, as a comparative example, the case where light irradiation is not performed, this is the same as that illustrated in FIG. 6.

As illustrated in FIG. 12, it can be seen that when intensity was at 30 $\mu W/cm^2$ or higher, the growth of *cladosporium* and *rhodotorula* was suppressed. Furthermore, it can be seen that when intensity was at 10 $\mu W/cm^2$ or lower, a suppressing effect on growth was obtained compared to when light irradiation was not performed.

Furthermore, even in the case (iv) where the samples were left standing for 46 hours after the last irradiation, almost no *cladosporium* and *rhodotorula* could be verified. It can be considered that irradiating with UV-B LIGHT destroyed the fungus such as *cladosporium* and *rhodotorula*. In particular, when the intensity of UV-B light was at 260 $\mu W/cm^2$ and 130 $\mu W/cm^2$, *cladosporium* and *rhodotorula* could not be verified by visual inspection, and are therefore considered sufficiently destroyed. On the other hand, when the intensity of UV-B light was at 60 $\mu W/cm^2$ and 30 $\mu W/cm^2$, a small amount of *cladosporium* and *rhodotorula* was verified. From this, it can be seen that the higher the intensity of UV-B light, the higher the bactericidal effect was.

Based on the above, it can be seen that by irradiating with UV-B light, *cladosporium* and *rhodotorula* can be destroyed. Therefore, for example, by switching between violet light irradiation and UV-B light irradiation, simple growth suppression (that is, without destroying or causing extinction of fungi/bacteria) and fungi/bacteria destruction can be used appropriately depending on the intended use.

For example, when violet light irradiation is insufficient and *cladosporium* and *rhodotorula* grow, irradiating with UV-B light can destroy the *cladosporium* and *rhodotorula* that have grown. Henceforth, even when fungi/bacteria such as *cladosporium* and *rhodotorula* reappear, their growth can be suppressed by regularly carrying out violet light irradiation.

Advantageous Effects, Etc

As described above, in the disinfecting method according to this embodiment, the light with which fungi/bacteria is irradiated includes UV-B light having a light emission peak whose peak wavelength is included in a range of from 280 nm to 350 nm, inclusive.

Accordingly, since the light with which fungi/bacteria is irradiated includes UV-B light, it is possible cause extinction of fungi/bacteria. For example, fungi/bacteria growth suppression by violet light irradiation and fungi/bacteria destruction or extinction by UV-B light irradiation can be used appropriately depending on the situation. Therefore, since it is possible to appropriately use the levels of disinfection such as whether to cause extinction of fungi/bacteria or whether to control fungi/bacteria growth (inhibit proliferation), the versatility of the disinfecting method can be further enhanced.

Furthermore, since a photocatalyst is not used, there is no need to apply a photocatalyst in advance, and use in a place where a photocatalyst cannot be applied is possible. In this manner, according to this embodiment, a versatile disinfecting method can be provided.

Furthermore, this embodiment shows an example in which violet light source 211 and UV-B light source 212 are lighted up mutually exclusively at different timings, the timing is not limited to such. Specifically, violet light source 211 and UV-B light source 212 may be lighted up at the same time. In other words, disinfecting apparatus 200 may irradiate fungi/bacteria with light including violet light and UV-B light.

Furthermore, it is acceptable for light source 210 to include only a single (or a single type of) LED. The LED may emit light including violet light and UV-B light. For example, the LED may emit light with a wide wavelength band ranging from the ultraviolet region to the visible light region.

Embodiment 3

In a disinfecting method according to Embodiment 3, a visible light-activated photocatalyst which is activated by violet light is used. As such, the disinfecting effect can be further enhanced. Furthermore, although versatility may deteriorate somewhat due to the need for preparations such as applying the photocatalyst in advance, versatility can be enhanced in the same manner as Embodiment 1 in terms of not having to use ultraviolet light. Hereinafter, details of the disinfecting method according to this embodiment and a disinfecting system which executes the disinfecting method will be described.

[Disinfecting System]

Figure 13:
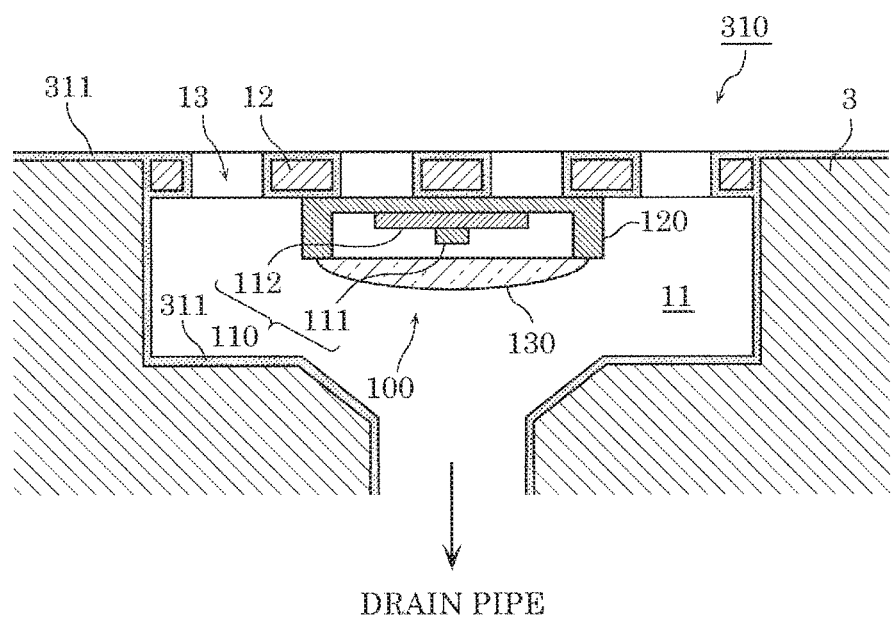
FIG. 13 is a cross-sectional view of a drainage port to which a disinfecting apparatus according to Embodiment 3 is installed.

FIG. 13 is a cross-sectional view of drainage port 310 to which disinfecting apparatus 100 according to this embodiment is installed. The disinfecting system according to this embodiment is applied to drainage port 310.

As illustrated in FIG. 13, the disinfecting system includes disinfecting apparatus 100 and photocatalyst 311. Disinfecting apparatus 100 is the same as described in Embodiment 1.

Photocatalyst 311 is provided in a part where fungi/bacteria tend to appear. Specifically, photocatalyst 311 is disposed adjacent to the fungi/bacteria that have appeared.

For example, photocatalyst 311 is applied to the surface of a component that is exposed in a damp place such as bathroom 1 or in a humid place such as ceiling spaces or under floors.

Specifically, photocatalyst 311 is applied to the surface of the component that is the irradiation target of the light irradiation by disinfecting apparatus 100. In the example illustrated in FIG. 13, photocatalyst 311 is applied to an exposed portion in water catching space 11 of drainage port 310. Specifically, photocatalyst 311 is applied to the surface of a floor component included in drainage port 310, the top surface and underside of lid 12, and the wall faces of through hole 13.

It should be noted that, in FIG. 13, photocatalyst 311 is also applied to the surface of floor 3. As such, when illumination apparatus 20 illustrated in FIG. 1 functions as disinfecting apparatus 100, the disinfecting effect according to this embodiment can be realized on the surface of floor 3. Furthermore, photocatalyst 311 may be applied to the light exit face of optical component 130.

Photocatalyst 311 is a material that is activated when irradiated with violet light. For example, photocatalyst 311 is a visible light-activated photocatalyst, and includes tungsten trioxide ($WO_3$).

It should be noted that photocatalyst 311 is exemplified as being applied and fixed to a floor component, etc., in this embodiment, but is not limited to such. For example, photocatalyst 311 may be sprayed in water catching space 11 and the space inside bathroom 1 using an atomizer, etc.

Furthermore, when disinfecting apparatus 100 emits ultraviolet light such as UV-B light or UV-A light, photocatalyst 311 may be an ultraviolet light-activated photocatalyst. For example, photocatalyst 311 may include titanium dioxide ($TiO_2$), etc.

[Experiment Results]

Next, the results of an experiment performed in order to study the relationship between the wavelength of light with which fungi/bacteria and photocatalyst 311 are irradiated and the growth of the fungi/bacteria will be described.

Figure 14:
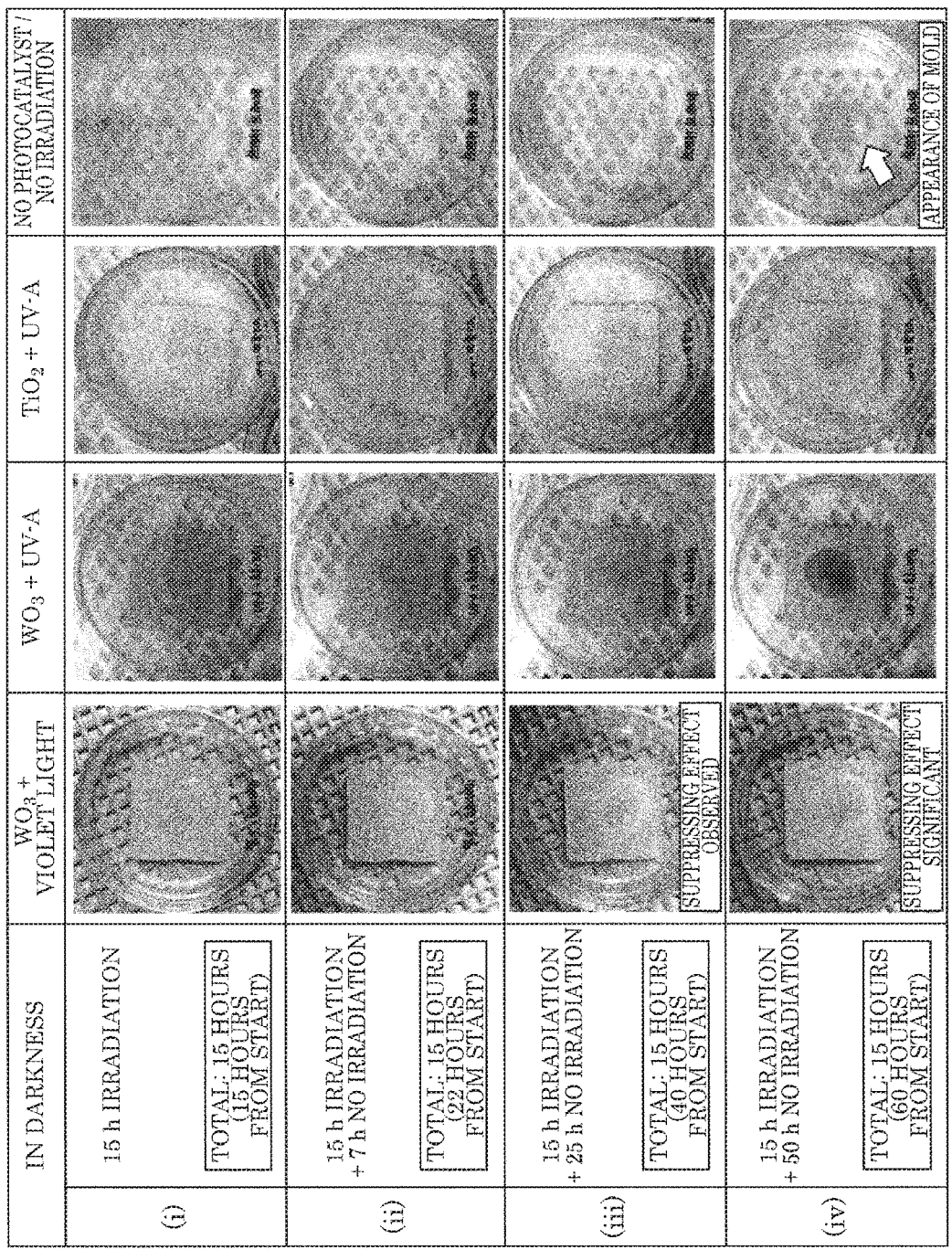
FIG. 14 is a chart illustrating results of observing fungi/bacteria in the case where the fungi/bacteria are irradiated with light using a photocatalyst according to Embodiment 3.

FIG. 14 is a chart illustrating the results of observing fungi/bacteria in the case where photocatalyst 311 according to this embodiment was used, and the fungi/bacteria were irradiated with light. Here, the fungi/bacteria observation conditions are as indicated below.

As observation subjects, a solution containing a predetermined amount of *cladosporium* and *rhodotorula* is dripped onto the surface of a base material (square shaped) to which photocatalyst 311 has been applied, and irradiated with light for a predetermined period then left standing with no irradiation. Furthermore, the case where photocatalyst 311 is not applied and light irradiation is not performed is also shown as a comparative example.

In this experiment, violet light having the spectral distribution illustrated in FIG. 4 and UV-A light having the spectral distribution illustrated in FIG. 5 are used as light with which the fungi/bacteria and photocatalyst 311 are irradiated. Specifically, when photocatalyst 311 is tungsten trioxide, irradiation with each of violet light and UV-A light was performed. When photocatalyst 311 was titanium dioxide, irradiation with UV-A light was performed. The irradiation light intensity was at 15 $\mu W/cm^2$ in the case of violet light and at 270 $\mu W/cm^2$ in the case of UV-A light. It should be noted that these values were the values measured using a Topcon UVR2.

(i) The first observation was performed after light irradiation was performed for the first 15 hours (i.e., at the point in time when total irradiation time was 15 hours, and 15 hours had elapsed from the start).

(ii) The second observation was performed at the point in time when 7 hours of non-irradiation had elapsed after the first observation (i.e., at the point in time when total irradiation time was 15 hours, and 22 hours had elapsed from the start).

(iii) The third observation was performed at the point in time when 25 hours of non-irradiation had elapsed after the first observation (i.e., at the point in time when total irradiation time was 15 hours, and 40 hours had elapsed from the start).

(iv) The fourth observation was performed at the point in time when 50 hours of non-irradiation had elapsed after the first observation (i.e., at the point in time when total irradiation time was 15 hours, and 65 hours had elapsed from the start).

As illustrated in FIG. 14, it can be seen that, by using photocatalyst 311, the fungi/bacteria were decomposed in the portion of the solution containing fungi/bacteria which was in contact with photocatalyst 311 (specifically, the bottom portion of the solution). When photocatalyst 311 is tungsten trioxide, a disinfecting effect is obtained in both the cases of violet light and UV-A light. When photocatalyst 311 was titanium dioxide 311, a disinfecting effect was obtained by irradiation with UV-A light.

On the other hand, since the decomposing effect of photocatalyst 311 was not exhibited in the top portion of the solution, appearance of *cladosporium* was verified in the samples irradiated with UV-A light. In contrast, in the sample irradiated with violet light, *cladosporium* could not be verified by visual inspection. This is the same as the results illustrated in FIG. 6 described in Embodiment 1.

Advantageous Effects, Etc

As described above, in the disinfecting method according to this embodiment, in the irradiating, photocatalyst 311 disposed adjacent to the fungi/bacteria is additionally irradiated with the light.

Accordingly, by activating photocatalyst 311, fungi/bacteria present in the vicinity of photocatalyst 311 can be decomposed. Therefore, the disinfecting effect can be further enhanced.

Furthermore, for example, photocatalyst 311 is a tungsten oxide.

Accordingly, since tungsten trioxide is excited by violet light, ultraviolet light need not be used. Therefore, components using a resin material, etc., having no ultraviolet light resistance can be irradiated with violet light. In this manner, according to this embodiment, a versatile disinfecting method can be provided.

It should be noted that tungsten trioxide is activated when irradiated with light having a wavelength of at most 450 nm. Therefore, although examples in which tungsten trioxide is irradiated with violet light or UV-A light are shown in this embodiment, the excitation light is not limited to such. The tungsten trioxide may be irradiated with LUV-B light (having the spectral distribution in FIG. 11, for example). Alternatively, the tungsten trioxide may be irradiated with light including UV-B light and violet light. Furthermore, the titanium dioxide may be irradiated with UV-B light.

Others

Although the disinfecting method and the apparatus according to the present disclosure are described based on the foregoing embodiments, etc., the present invention is not limited to the foregoing embodiments.

For example, the fungi/bacteria which are the subjects of disinfection are exemplified as *cladosporium, rhodotorula,* and *Pseudomonas aeruginosa* in the foregoing embodiments, but are not limited to such. For example, violet light irradiation may be performed on filamentous fungi which cause powdery mildew, blast, etc.

Furthermore, since the disinfecting methods and disinfecting apparatuses according to the foregoing embodiments are capable of suppressing the appearance of molds and yeasts, the appearance of insect pests that feed on molds and yeasts can also be suppressed. For example, the appearance of psocids which feed on molds and yeasts can be suppressed. With this, the appearance of cheyletids which feed on the psocids can additionally be suppressed.

In this manner, by suppressing the appearance of fungi/bacteria such as molds and yeasts, appearance of pests that do harm to the human body can be suppressed. Specifically, the disinfecting methods and disinfecting apparatuses in the respective embodiments indirectly have insect pest expelling and controlling effects.

Furthermore, for example, although an example in which violet light irradiation and non-irradiation are repeated is shown in the foregoing embodiments, the violet light irradiation is not limited to such. The violet light irradiation may be performed on the fungi/bacteria constantly. Furthermore, in the case of alternately repeating between irradiation and non-irradiation periods, the irradiation period may be different for each iteration. This is also true for the non-irradiation period.

Furthermore, for example, disinfecting apparatus 100 is exemplified as including battery 150 in the foregoing embodiments, but is not limited to such. Disinfecting apparatus 100 may have a power supply cord (plug) and be supplied with power from a commercial power source. Accordingly, it is possible to avoid not being able to perform disinfecting due to a dead battery.

Furthermore, for example, disinfecting apparatus 100 need not include control circuit 140, memory 160, and switch 170, etc. For example, disinfecting apparatus 100 may include a wireless communication module instead. Disinfecting apparatus 100 may receive a control signal for controlling the lighting-up and putting-out of light source 110 from an external controller (or a server device), etc., via wireless communication such as Wi-Fi (registered trademark), Bluetooth (registered trademark), etc. Disinfecting apparatus 100 may control the lighting-up and putting-out of light source 110 based on the control signal received.

It should be noted that, for example, disinfecting apparatus 100 is exemplified as being installed in drainage port 10 of bathroom 1 in the foregoing embodiments, but is not limited to such. Disinfecting apparatus 100 can be applied in all environments that can come into contact with water or vapor.

For example, disinfecting apparatus 100 can be used in ordinary homes such as a house. Specifically, disinfecting apparatus 100 may be installed in wet area facilities such as toilets, kitchens, wash basins, drain pipes, etc. Alternately, disinfecting apparatus 100 may be installed in locations where condensation tends to occur such as under floors, in ceiling spaces, window sashes, etc. Furthermore, disinfecting apparatus 100 may be installed in poorly ventilated shoe cabinets, clothes chests, closets, etc.

Furthermore, for example, disinfecting apparatus 100 may be installed in electrical appliances. Specifically, disinfecting apparatus 100 may be installed in dishwashers, washing machines, refrigerators, rice cookers, alkali ion water purifiers, vacuum cleaners, or air conditioning equipment such as ventilating fans, dehumidifiers, driers, humidifiers, etc.

Furthermore, for example, disinfecting apparatus 100 can also be used in the fields of agriculture, fishery, and livestock. Specifically, disinfecting apparatus 100 may be installed in plastic greenhouses, food processing plants, slaughterhouses, fish delivery centers, wholesale markets, etc. For example, food processing plants include processing plants for various food products such as canned goods, cut vegetables, powdered foodstuff, liquor, frozen food, etc. Furthermore, disinfecting apparatus 100 can be used in plant factories using artificial light, in protected horticulture using both artificial light and sunlight, as outdoor lamps for outdoor cultivation, etc.

Furthermore, for example, disinfecting apparatus 100 can also be used in the field of industry. For example, disinfecting apparatus 100 may be installed in drainage equipment, etc., of semiconductor wafer manufacturing plants, etc.

Furthermore, for example, disinfecting apparatus 100 can be installed in the various edifices of various institutions such as office buildings, hospitals, nursing homes, supply centers for school meals, schools, etc. Furthermore, for example, disinfecting apparatus 100 may be installed in eating establishments such as cafes, restaurants, bars, etc., or stores of retailers such as flower shops, pet shops, etc. Furthermore, for example, disinfecting apparatus 100 may be installed in the food sections of supermarkets or department stores. Specifically, disinfecting apparatus 100 may be used near the fresh fish corner or refrigeration facilities including the ceiling.

It should be noted that, in the same manner, disinfecting apparatus 200 according to Embodiment 2 and disinfecting apparatus 100 which uses photocatalyst 311 according to Embodiment 3 can also be applied to all the environments that can come into contact with water or vapor exemplified above.

Furthermore, in each of the foregoing embodiments, structural components such as control circuit 140, memory 160, and switch 70 may be configured using dedicated hardware or may be implemented by executing software programs suitable for the respective structural components. Each of the structural components may be implemented by a program executing component, such as a central processing unit (CPU) or processor, reading and executing a software program recorded on a recording medium such as a hard disc or a semiconductor memory.

It should be noted that the present invention can be implemented not only as a disinfecting apparatus but also as a program which includes, as steps, the processes performed by the respective structural components of the disinfecting apparatus, and a computer-readable recording medium on which such program is recorded, such as a digital versatile disc (DVD), etc.

Specifically, the above-described generic or specific aspects may be implemented as a system, an apparatus, an integrated circuit, a computer program, and a computer-readable recording medium, and may be implemented by an arbitrary combination of a system, an apparatus, an integrated circuit, a computer program, and a recording medium.

Forms obtained by various modifications to the embodiment that can be conceived by a person of skill in the art as well as forms realized by arbitrarily combining structural components and functions in the embodiment which are within the scope of the essence of the present invention are included in the present invention.

What is claimed is:

1. A disinfecting method comprising:
   irradiating one of a fungus and a bacterium with light including violet light having a light emission peak with (i) a full width at half maximum of at most 20 nm and (ii) a peak wavelength greater than 380 nm and less than 400 nm
   wherein the light does not include UV-A light having a light emission peak with a peak wavelength included within an entire range of from 350 nm to 380 nm, inclusive, and does not include, in a wavelength range from 350 nm to 450 nm, inclusive, a light emission peak with a light emission intensity greater than the light emission intensity at the light emission peak of the violet light.

2. The disinfecting method according to claim 1, wherein the light further includes UV-B light having a light emission peak with a peak wavelength included in a range of from 280 nm to 350 nm, inclusive.

3. The disinfecting method according to claim 1, wherein in the irradiating, irradiation with the violet light and non-irradiation are repeated.

4. The disinfecting method according to claim 1, wherein the fungus is one of *cladosporium* and *rhodotorula*.

5. The disinfecting method according to claim 1, wherein the bacterium is *Pseudomonas aeruginosa*.

6. The disinfecting method according to claim 1, wherein in the irradiating, a photocatalyst disposed adjacent to the one of the fungus and the bacteria is additionally irradiated with the light.

7. The disinfecting method according to claim 6, wherein the photocatalyst is a tungsten oxide.

8. A disinfecting apparatus comprising:
   a light source which irradiates one of a fungus and a bacterium with light having a light emission peak with (i) a full width at half maximum of at most 20 nm and (ii) a peak wavelength greater than 380 nm and less than 400 nm,
   wherein the light does not include UV-A light having a light emission peak with a peak wavelength included within an entire range of from 350 nm to 380 nm, inclusive, and does not include, in a wavelength range from 350 nm to 450 nm, inclusive, a light emission peak with a light emission intensity greater than the light emission intensity at the light emission peak of the violet light.

9. The disinfecting apparatus according to claim 8, further comprising:
   an optical filter which is disposed between the light source and the one of the fungus and the bacterium, and removes, from the light, wavelength components in a range of from 350 nm to 380 nm, inclusive.

10. The disinfecting apparatus according to claim 8, wherein
    the light further includes UV-B light having a light emission peak with a peak wavelength included in a range of from 280 nm to 350 nm, inclusive.

11. The disinfecting apparatus according to claim 8, wherein
    the light source repeats irradiation with the violet light and non-irradiation.

12. The disinfecting apparatus according to claim 8, wherein
    the fungus is one of *cladosporium* and *rhodotorula*.

13. The disinfecting apparatus according to claim 8, wherein
    the bacterium is *Pseudomonas aeruginosa*.

14. The disinfecting apparatus according to claim 8, wherein
a photocatalyst is disposed adjacent to the one of the fungus and the bacteria, and the photocatalyst is additionally irradiated with the light.

15. The disinfecting apparatus according to claim 14, wherein
the photocatalyst is a tungsten oxide.

16. The disinfecting method according to claim 1, wherein the light has a full width at half maximum of approximately 10 nm and a peak wavelength of 390 nm.

17. The disinfecting apparatus according to claim 8, wherein the light has a full width at half maximum of approximately 10 nm and a peak wavelength of 390 nm.

18. The disinfecting method according to claim 1, further comprising:
positioning an optical filter between a light source of the irradiating light and the one of the fungus and the bacterium, and removing, from the irradiating light, by the optical filter, wavelength components in an entire range of from 350 nm to 380 nm, inclusive, the optical filter not removing from the irradiating light, wavelength components greater than 380 nm and less than 350 nm.

19. The disinfecting method according to claim 1, further comprising, disposing an optical filter between a source of the light and the one of the fungus and the bacterium, the optical filter removing, from the light, wavelength components in a range of from 350 nm to 380 nm, inclusive.

* * * * *